United States Patent [19]

Wallenfels et al.

[11] Patent Number: 4,716,222
[45] Date of Patent: Dec. 29, 1987

[54] SUBSTRATES FOR HYDROLASES

[75] Inventors: Kurt Wallenfels, Freiburg, Fed. Rep. of Germany; Ahmed M. Fathy, Heliopolis, Egypt

[73] Assignee: Hoechst Aktiengesellschaft, Frankfurt am Main, Fed. Rep. of Germany

[21] Appl. No.: 720,347

[22] Filed: Apr. 5, 1985

[30] Foreign Application Priority Data

Apr. 6, 1984 [DE] Fed. Rep. of Germany ....... 3412939

[51] Int. Cl.⁴ .............................................. C07H 17/02
[52] U.S. Cl. .................................. 536/18.7; 536/18.1; 536/120
[58] Field of Search ....................... 536/4.1, 18.6, 120, 536/18.1, 18.7

[56] References Cited

U.S. PATENT DOCUMENTS

| | | | |
|---|---|---|---|
| 2,616,889 | 11/1952 | Velluz et al. | 536/18.1 |
| 3,547,828 | 12/1970 | Mansfield et al. | 536/4.1 |
| 4,038,270 | 7/1977 | Higashiyama et al. | 536/18.6 |

FOREIGN PATENT DOCUMENTS

A2-0156347  3/1985  European Pat. Off.

*Primary Examiner*—J. R. Brown
*Assistant Examiner*—Elli Peselev
*Attorney, Agent, or Firm*—Finnegan, Henderson, Farabow, Garrett and Dunner

[57] ABSTRACT

Chromogenic substrates of the formula A—O—B are described, in which A represents the radical in the ion A—O⁻ of a compound A—OH, whose absorbance is measured photometrically after hydrolysis of A—O—B, while B is the radical in a compound B—OH which makes the compound specific for the reaction with a given enzyme, and where A—OH is a hydroxynitropyridine, a hydroxynitrobenzopyranone, a dibenzox(or thi)azine or a dibenzopyranone or a derivative thereof, and B is a sugar or sugar derivative, an amino acid or an oligopeptide or an inorganic acid.

These compounds can be used for the detection and determination of hydrolases.

12 Claims, No Drawings

SUBSTRATES FOR HYDROLASES

The invention relates to substrates for the determination of hydrolases, a method for their preparation, their use for the determination of hydrolases and suitable means for that purpose.

The detection or the determination of hydrolases is of interest for the diagnosis and monitoring the progress of various disorders. Examples are the determination of amylase for pancreatic diagnosis and of acid phosphatase for the detection of prostatic carcinoma (review in R. J. Haschen, Enzymdiagnostik, [Enzyme diagnosis] Gustav Fischer Verlag, Stuttgart, 1970), of esterases as indicators for leukocytes (EP-A-12,957) or of phosphatase or galactosidase in enzyme immunoassay as indicators for immunological methods of determination.

Currently the determinations of hydrolases which have a pH optimum of less than 7 are generally carried out photometrically by two-point measurement.

Generally, two-point determinations require a longer time than determinations which can be carried out kinetically and furthermore they are not practical for the widely used autoanalyzers, so that only the expensive manual determination is possible. Moreover, they are less precise than the kinetic methods and are more difficult to be surveyed, which can lead to incorrect results.

The few feasible kinetic determinations of hydrolases with an acid pH optimum require multistage reactions, as described for example for acid phosphatase in German Pat. No. 2,115,748, or use fluorogenic substrates, such as for example derivatives of 4-methylumbelliferone. However, multi-state reactions lead to interference with the determination by impurities in the reagents, especially in the auxiliary enzymes, and to competing reactions with constituents of biological fluids. Moreover, they increase the cost of the method. Fluorescence can only be evaluated with special instruments, standardization is difficult and it tends to change under various influences, thus rendering poor precision and incorrect results. Furthermore, fluorogenic substrates are not suitable for the evaluation of enzyme activity under conditions of substrate saturation since the fluorescence of the originating reaction product is considerably quenched at high concentrations of the fluorogenic substrate. Elaborate correction and standardizing procedure would be required in order to obtain appropriate results.

Also, methods are already known for the determination of α-amylase activity using p-nitrophenyl-α-maltodextrins, for example Testomar ®-Amylase, Behringwerke AG, Federal Republic of Germany, where the determination is carried out kinetically at pH 7, which has the disadvantage of the marked pH-dependence of the extinction coefficient of the liberated nitrophenol and makes the test susceptible to interference. Moreover, some 50% of the sensitivity is lost when the nitrophenyl group is the chromogen, since the molar extinction coefficient of nitrophenol, for example at pH 7, is only half as high as at pH 9. However, it is not possible to determine the activity of amylase at pH 9, since under these conditions it loses its activity.

Moreover, hitherto all amylase determinations carried out kinetically (German Offenlegungsschrift No. 275,201, German Offenlegungsschrift No. 2,731,372, German Offenlegungsschrift No. 2,822,364, German Offenlegungsschrift No. 3,000,292, Japanese Pat. No. 113,138) are multi-stage reactions, requiring one or more auxiliary enzymes. This is associated with the disadvantage already described above.

The sensitivity of the detection system is crucial in determinations of trace components in biological fluids. Thus, recently enzyme immunoassays have been developed in addition to the radioimmunoassay. They permit the detection of trace amounts of proteins in human serum for example galactosidase in the indicator reaction.

However, the current methods all have the disadvantage of incubation periods of one or more hours. With an increased sensitivity of the indicator reaction it would be possible either to reduce the incubation period or to increase the sensitivity within given incubation period.

Esterases are diagnostic parameters for the presence for leukocytes. Nowadays, in addition to the specificity a high degree of sensitivity is also necessary, so that the result can be read after only a few minutes reaction time. For a visually assessable test system, such as, for example, test strips, dyes which produce the optimal color indicators for the human eye (red, green, blue) are necessary. The yellow color of nitrophenol or nitroaniline is in this respect very unfavorable. Therefore the attainable sensitivity depends critically on the chromogenic moiety of the substrate molecule.

The chromogenic substrates of the present state of art are unsuitable for visual evaluation either because of the resulting color (yellow) or because of their low reactivity. Thus, for example, with the chromogenic amino acid esters as disclosed in the European Pat. Nos. 0,007,407 (sulfophthaleins), 0,008,438 (azo dyes), 0,012,957 (indoxyl) or German Pat. No. 3,005,845 (indoanilines), which all of which procedure coloration being easily evaluable by visual inspection, the sensitivity is as good as the lower limit of 2 to 5 leukocytes/µl, detectable within the demanded 2 min. for color development, is obtained. For diagnosis, however, a much lower limiting value is desirable. An increase of the sensitivity is achieved by supplementing accelerators to the chromogenic substrates.

U.S. Pat. No. 3,378,463 describes the fluorescence of esterase substrates with chromogens of the indoxyl and resorufin type, which, however, can only be used when evaluation is with the appropriate instruments (fluorometers). An interesting statement is found in column 5, lines 61 to 65 of this patent: corresponding indoxyl derivatives are cleaved much faster than the resorufin derivatives. With reference to that what is said before it was to be expected that the resorufin esters would show even less sensitivity in the detection of esterase from leukocytes, for example.

Another disadvantage of the substrates described in the above mentioned patent is their reactivity towards other esterases. Not only esterases, such as cholinesterase, acylase, lipase or acid phosphatase react with resorufin acetate and resorufin butyrate, but also proteases such as chymotrypsin (Table III of the U.S. Pat. No. 3,378,463).

The subject of the invention was to disclose sensitive indicators for enzyme reactions, liberating an anionic dye by enzymatic hydrolysis (dye is understood here to be a compound with an absorption between 300 and 760 µm) having the lowest possible $pK_a$ and the highest possible molar absorbtivity, furtheron referred to as molar extinction coefficient, of the anion in order thus to make possible a kinetic determination of hydrolases which can be carried out using auto-analyzers or to make it possible to design a more sensitive indicator reaction for enzyme immunoassays. Another object was to make available enzyme substrates which react specifically with only one enzyme and therefore permit in a mixture of enzymes, such as is found in biological fluids, a specific determination of one enzyme or of a group of enzymes.

It has now been found, surprisingly, that the compounds of the general formula A—O—B, in which A represents the radical in the ion A—O⁻ of a heterocyclic compound A—OH with an acid $pK_a$, whose extinction is measured photometrically after hydrolysis of A—O—B, while B is the radical in a compound B—OH which makes the compound specific for the reaction with a given enzyme, and where A—OH is a. a compound of the general formula I

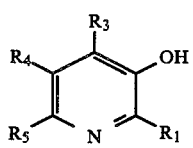

in which $R_1$ can be OH, $NO_2$ or halogen, and $R_3$, $R_4$ and $R_5$ can be H or $NO_2$, at the most two $NO_2$ being present, b. a compound of the general formula II

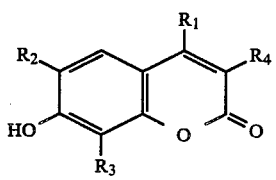

in which $R_1$ can be H or alkyl with 1-12, preferably 1-3, carbon atoms, and $R_2$, $R_3$ or $R_4$ can be H or $NO_2$, one or two $NO_2$ being present, c. a compound of the general formula III

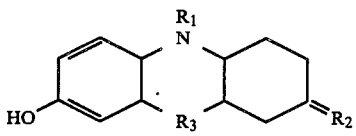

in which $R_1$ can be O or an electron pair, $R_2$ can be O, S or $N(CH_3)_2$, and $R_3$ can be O or S or d. a compound of the general formula IV

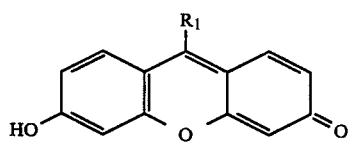

in which $R_1$ can be aryl, preferably phenyl, CN or alkyl with 1-12, preferably 1-3, carbon atoms, and B—OH is a sugar or sugar derivative, in particular glucose, a maltodextrin, galactose, glucuronic acid, N-acetylglucosamine or fucose, an amino acid or an oligopeptide, each of which can carry a protective group, particularly the toluenesulfonyl or carbobenzyloxy (CBZ) group, in particular N-tosylalanine or is CBZ-glycine, or is an inorganic acid, in particular phosphoric acid or sulfuric acid, are substrates with a high detection sensitivity for the determination of hydrolases.

The invention therefore relates to a compound of the formula A—O—B and the given definitions, to a method for its preparation, as well as to its use for the determination of a hydrolase.

Substrates which are particularly suited for the kinetic determination of hydrolases with a pH optimum of less than 7 are those whose hydrolysis liberates a dye with a $pK_a$ under 7. The dyes used exhibit an intense color even at a pH of less than 7 and accordingly can be sensitively detected by photometry or with the naked eye.

There was a bias against the feasibility of a synthesis of glycosides with aglycons having 'a low pKa' i.e. with comparatively acidic aglycons, since for such glycosides a low thermodynamic stability was to be expected. Such compounds tend to have the characteristics of anhydrides, which are wellknown to be considerably less stable thermodynamically than normal glycosides and esters.

Surprisingly, however, it was found that derivatives of the heterocyclic substances specified above, which have a low $pK_a$ compared with the isocyclic compounds hitherto used for the synthesis of glycosides and esters such as, for example, 2,4-dinitrophenyl galactoside, have sufficient kinetic stability to enable satisfactory yields to be obtained.

A further surprising property of these compounds was that they showed relatively sharp, and in some cases very high absorption bands at long wavelengths, which makes them particularly suited as indicators for the widely used measurement by absorption photometry.

Moreover, it is true for the compounds described that they are particularly quickly cleaved by the hydrolases whose substrates they are intended to be, although the dye components show no similarity with the analogous natural substrate constituents (aglycone moiety in disaccharides or starch, alcohol component of esters). This was not to be expected.

The substrates with the general formula A—O—B were prepared in three stages:

1. Preparation of the moiety AOH, namely the dye,
2. Preparation of the moiety BOH, namely a carbohydrate or carbohydrate derivative or an acid, and
3. Preparation of the substrate A—O—B from AOH and BOH using a method which, particularly with the carbohydrates and carbohydrate derivatives, produces a substrate with the desired stereoisomerism.

The known dyes can be prepared by the following methods: nitropyridine and nitrocoumarin derivatives generally by nitration of the corresponding parent compounds in sulfuric acid solution at a temperature of 0° C. by the dropwise addition of an $HNO_3/H_2SO_4$ mixture (Shah and Mehta, J. Indian Chem. Soc. (1954), 784; Pechman and Obermueller, Ber. 34 (1901), 660; Chakrawarti, J. Indian Chem. Soc. Ber. 34 (1901), 660; Chakrawarti, J. Indian Chem. Soc. 12 (1935), 791-795; Burton et al., J. Chem. Soc. Perin II (1972), 1953-1958; Brignell et al., J. Chem. Soc. (B) (1968), 1477; de Selems, J. Org. Chem. 33 (1968), 478; Talik andTalik, Rocziniki Chemii, Ann. Soc. Chem. Polonorum 40 (1966), 1187); Resazurin (10-oxide of 3H-7-hydroxyphenoxazin-3-one) according to Nietzki et al., Ber. der Deut. Chem. Ges. 22 (1889), 3020; Resorufin (3H-7-hydroxyphenoxazin-3-one) by reduction of resazurin with sodium borohydride; 6-hydroxy-9-phenyl-3H-xanthen-3-one according to Nathsen, J. Amer. Chem. Soc. 47 (1925), 1079; other phenoxazines and xanthenones according to Stuzka et al., Collection Czechoslov. Chem. Commun. Vol. 34 (1969), 221 or Kehrman and de Gottrau, Ber. 38 (1905), 2575.

3H-6-Hydroxy-9-cyanoxanthen-3-one, which we refer to as cyanorufin in the following text, is new. It was prepared by the method described in the Examples.

Also new is 7-hydroxy-3-nitrocoumarin, which was prepared by the ring closure of a nitrostyrene derivative. It has a melting point of 192°-198° C. and an absorption maximum of 450 nm at pH>8, while at pH<6 the absorption maximum is at 390 nm.

The known derivatives of the carbohydrate B—OH which carry protective groups if necessary and are suitable for the preparation of the compounds of the formula A—O—B by reaction which A—OH were prepared according to Methods in Carbohydrate Chemistry, volume II, Academic Press 1963. The amino acids or oligopeptides provided with protective groups were bought, or were prepared according to Example 16 (J. Amer. Chem. (1937) 59, 1116-1118).

The new compounds of the formula A—O—B were prepared by methods known per se from a compound of the formula A—OH and a reactive derivative of a compound of the formula B—OH.

The compounds of the formula A—O—B can be used as substrates for the detection and the determination of hydrolases. The dye A—OH, which is liberated on cleavage, has appreciable advantages over those of the state of the art. While the $pK_a$ of the widely used dye p-nitrophenol, that is to say pH at which half of the p-nitrophenol is present in a dissociated form as phenolate anion, is 7, the $pK_a$ of the dye A—OH used by us is less than 6 (Table 1). This means that even in the pH range below 7 there is compared with p-nitrophenol, a considerably higher extinction at the same molarity, so that the new substrates prepared from these dyes can therefore be measured with considerably greater sensitivity.

In the text which follows the advantages of using the new substrates compared with those of the state of the art are described with the aid of Examples.

The activity of α-glucosidase in human urine can be determined very sensitively in a kinetic test with the new substrate 2H-7-0-(α-D-glucopyranosyl)-4-methyl-8-nitrobenzopyran-2-one (compound S1, see Example 1). Since the pH optimum of α-glucosidase is 4 to 6, the activity cannot be measured kinetically with the hitherto customary substrate p-nitrophenyl α-glucopyranoside because the released nitrophenol has only a very low extinction at 405 nm (Table 1).

TABLE 1

Extinction coefficients of examplarily selected dyes at different pH values

| Dye | pKa | Wavelength (nm) | Extinction coefficient ($1 \cdot mol^{-1} \cdot cm^{-1} \cdot 10^3$) pH 4.0 | 5.0 | 6.0 | 7.1 | 10 |
|---|---|---|---|---|---|---|---|
| 4-Methyl-8-nitrobenzopyran-2-one | 4.45 | 350[b] | 8.50 | 15.0 | 18.80 | 19.4 | 19.4 |
|  |  | 365[c] | 5.80 | 11.3 | 16.10 | 16.25 | 16.30 |
| 3-Hydroxy-2-nitropyridine | 5.1 | 405 | 0.50 | 2.32 | 5.09 | 5.80 | 5.90 |
| Resorufin | 5.95 | 578[b] | 0.75 | 5.7 | 22.80 | 39.6 | 41.000 |
|  |  | 574[c] | 1.00[a] | 7.4[a] | 29.64[a] | 49.87 | 55.42 |
| 3-Hydroxy-4-nitro-2-chloropyridine | 3.1 | 405 | 4.93 | 5.34 | 5.40 | 5.48 | 5.4 |
| 3-Hydroxy-2-nitro-6-chloropyridine | 3.9 | 365 | 7.84 | 11.87 | 12.9 | 13.2 | 13.2 |
| p-Nitrophenol | 7.0 | 405 | 0.20 | 0.40 | 1.50 | 9.7 | 18.30 |
| o-Nitrophenol | 7.08 | 405 | 0.47 | 0.48 | 0.75 | 2.34 | 4.01 |

[a]calculated
[b]variable wavelength photometer
[c]photometer equipped with a mercury lamp and filterd for fixed wavelengths An assay mixture containing this substrate must therefore, after a set reaction time, be made alkaline by additives such as bicarbonate in order to achieve a measurable extinction.

In contrast, with compound S1 as substrate an absorbance difference in normal human urine of 0,040 per minute could be measured in a kinetic test, and thus the automation of this determination is possible.

It is known that inhibitors which affect the activity of glucosidase can occur in urine. In this case the inhibitor must be removed by the use of suitable techniques, such as for example dialysis or gel filtration. The use of purified β-glucosidase showed that substrate S1 is a specific substrate for α-glucosidase since it is not cleaved by β-glucosidase.

A further possibility for the kinetic determination of α-glucosidase activity is the use of 3-H-7-O-(α-glucopyranosyl)phenoxazin-3-one (resorufin-α-D-glucopyranoside). It is true that the $pK_a$ of the resorufin is 5.9, but because of the very high molar extinction coefficient at 578 nm the urinary glucosidase can be determined at, for example, pH 6 with adequate sensitivity. At 37°, using 400 μl reagent and 200 μl urine an absorbance difference of 0.136 a per minute was found. Measurement at 578 nm has the advantage that the colored constitutents in urine do not interfere. Here also the use of β-glucosidase showed that resorufin-α-glucopyranoside is a specific substrate for α-glucosidase.

The determination of β-glucosidase activity in human urine has hitherto not been possible with the usual assays because of their limited sensitivity. Comparison measurements of β-glucosidase activity were carried out using 3-O-(β-D-glucopyranosyl)-3-hydroxy-2-nitropyridine (compound S5) and p-nitrophenyl β-D-glucopyranoside. The results for both are shown in Table 2 and prove that with the new substrate S5 an approximately 7-fold larger absorbance change per minute was found.

TABLE 2

Determination of β-glucosidase activity in a urine sample

| Substrate | Absorbance Difference/min T = 25° C. delta A/min |
|---|---|
| p-nitrophenyl derivative | 0,0476 |
| S5 | 0,332 |

For determination of α-amylase, the measured extinction changes were compared for the following new substrates: 2H-7-O-(α-D-maltotriosyl)-4-methyl-8-nitrobenzopyran-2-one (compound S10), the corresponding maltotetraosyl compound (compound S11) as well as o-nitrophenyl α-maltotrioside.

The measured absorbance change with substrate S11 was approximately 14-fold and that with substrate S10 was even 32-fold greater than with the nitrophenyl derivative (Table 3).

TABLE 3

Determination of α-amylase activity in a urine sample without auxiliary enzyme α-glucosidase

| Substrate | delta A/min |
|---|---|
| nitrophenyl derivative | 0,020 |
| S11 | 0,134 |
| S10 | 0,635 |

These high absorbance changes with the new substrates are achieved without the participation as an auxiliary enzyme of α-glucosidase which is required in the existing assay systems for the liberation of the dye. This does away with reagent costs and with further difficulties shown by all previous kinetic assays for amylase determination, namely the non-linear initial phase of the kinetics, which in general extends over several minutes. In contrast, on use of the new substrates the kinetics are linear from the start. Appreciably quicker measurement is thus possible manually and, in particular, with automatic analyzers.

Likewise, sufficiently high absorbance changes could be achieved with 3-O-(α-D-maltotriosyl)-3-hydroxy-2-nitropyridine (compound S12) in comparison with the state of the art but without participation of the auxiliary enzyme α-glycosidase and with immediately linear kinetics.

The activity of the β-galactosidase in human urine could be kinetically determined by the use of 3-O-(α-D-galactopyranosyl)-3-hydroxy-2-nitropyridine. For this purpose 0.2 ml of 10-fold concentrated normal urine was added to 1 ml of buffered substrate solution and the extinction change recorded at 405 nm and 22° C. Under these conditions an extinction difference of 1.2 mE/min was measured. This substrate is not cleaved by β-galactosidase.

The β-galactosidase activity could be kinetically measured in human urine by the use of 2H-7-O-(β-D-galactopyranosyl)-4-methyl-8-nitrobenzopyran-2-one (compound S15). An extinction change of 4 mE/min was recorded at 23° C. and 366 nm with the use of 200 μl of buffered substrate solution and 200 μl of urine of normal concentration. The substrate is not cleaved by β-galactosidase. Also, β-galactosidase in human urine could be kinetically determined by using resorufin-β-D-galactopyranoside (compound S6). In this case an absorbance change at 578 nm of 0,0038 A/min was achieved at 37° C. The activity of β-glucuronidase in human urine could be kinetically measured with 2H-7-O-(β-D-glucuronopyranosyl)-4-methyl-8-nitrobenzopyran-2-one (compound S9).

In this case, 0.1 ml of urine concentrate was added to 0.6 ml of buffered substrate solution and the activity recorded at pH 5, 30° C. and 366 nm. Under these conditions an absorbance difference of 0,014 A/min was measured. Consequently the determination is many times more sensitive than with the customary p-nitrophenyl substrate (Table 4).

TABLE 4

Determination of β-glucuronidase in human urine at pH 5

| Substrate | delta A /min |
|---|---|
| Compound S9 | 0,014 |
| p-nitrophenyl substrate | 0,0005 |

The sensitivity of the substrates p-nitrophenyl N-acetylaminoglucoside and 2H-7-O-(2-acetamido-2-deoxy-D-glucopyranosyl)-4-methyl-8-nitrobenzopyran-2-one (compound S9) were compared to each other using N-acetyl-β-glucosaminidase from ox kidney. To 0.5 ml of substrate solution was added 0.1 ml of an enzyme solution diluted 1:101 (Sigma) and the absorbance change determined at 22° C. and 405 or 365 nm. The results are summarized in Table 5.

The absorbance change at the set pH of 4.5 is some 36-fold greater for S8 than with p-nitrophenyl acetylaminoglucoside.

The activity in human urine (10-fold concentrated) can also be kinetically determined with S8. The determination with 0.5 buffered substrate solution and 0.1 ml 10-fold concentrated normal urine at 37° C. and 365 nm gave an absorbance change of 0,023 A/min at pH 5.5 and of 0,014 A/min at pH 4.5.

These extinction changes are so large that the activity could also be kinetically measured with sufficient sensitivity in the same sample volume of undiluted urine.

TABLE 5

Determination of N—acetylglucosaminidase

| Substrate | delta A/min |
|---|---|
| p-nitrophenyl substrate | 0,0076 |
| compound S8 | 266 |

The activity of acid phosphatase could be kinetically determined substantially more sensitively with 2H-7-O-4-methyl-8-nitrobenzopyran-2-one phosphate (compound S13) than with nitrophenyl phosphate. The determination was carried out in seminal plasma, diluted 1:101 using both substrates. 0.01 ml of diluted sample was added to 1 ml of a buffered substrate solution, pH 4.8 and the extinction changes kinetically recorded at 405 or 365 nm.

As Table 6 shows, the absorbance change with S13 is about 13-fold greater than for nitrophenyl phosphate.

TABLE 6

| Substrate | delta A/min | Ratio of the absorbance changes |
|---|---|---|
| Compound S13 | 0,0975 | 13 |
| p-nitrophenyl phosphate | 0,0075 | 1 |

The invention also relates to a diagnostic means for the detection of esterolytic enzymes, in particular for the detection of esterases in leukocytes, composed of an absorptive carrier, a film layer, a loose or compacted powder mixture, a lyophilized composition or a solution, containing one or more compounds of the formula A—O—B, in which AOH is a dye of the general formula III or IV and BOH is an amino acid or an oligopeptide, provided if necessary with a protective group, and usual additives such as buffer substances, detergents, activators or inhibitors or/and stabilizers.

Furthermore the present invention relates to the use of one of the compounds of the formula A—O—B presented in the preceding section for the preparation of a diagnostic means for the detection of esterolytic enzymes, in particular the esterases occurring in leukocytes, in body fluids.

In general, with the enzyme immunoassay the intention is to detect substances which are present in a very low concentration. The sensitivity of this detection system is therefore of great significance.

A substantial increase in sensitivity could be achieved using the new substrates in an enzyme immunoassay of the state of the art. In this assay the IgE concentration is determined, as a measure of an allergy by means of the indirect antibody technique. With the same incubation periods for the different substrates, an approximately 4.3-fold higher absorbance for resorufin-$\beta$-galactoside (compound S6) and an approximately 1.7-fold higher absorbance for 3-hydroxy-2-nitropyridine-$\beta$-galacto-side was measured than for the commercially available o-nitrophenyl-$\beta$-galactoside.

Therefore, with resorufin-$\beta$-glactoside the incubation period for the enzyme reaction can be substantially shortened obtaining the same sensitivity, or, the sensitivity for the IgE detection can be considerably increased at the prior used incubation periods. Both steps may be of great practical importance. It depends on the substance to be detected whether a higher sensitivity or a quicker assay result is more important.

TABLE 7

Determination of IgE in the same sample with a state of the art enzyme immunoassay using one commercially available and two new substrates.

| Substrate | Measuring wavelength | Absorbance change |
| --- | --- | --- |
| Resorufin-$\beta$-galactoside | 576 nm | 0.761 |
| 3-Hydroxy-2-nitropyridine-$\beta$-galactoside | 405 nm | 0.298 |
| o-Nitrophenyl galactoside | 405 nm | 0.176 |

The following examples are intended to illustrate the invention.

EXAMPLE 1

2H-7-O-($\alpha$-D-Glucopyranosyl)-4-methyl-8-nitrobenzopyran-2-one (compound S1)

17 g of 1-$\beta$-chloro-3,4,6-triacetyl glucopyranoside were heated under reflux, and with exclusion of moisture, with 15 g of 2H-7-hydroxy-4-methyl-8-nitrobenzopyran-2-one in toluene for 20 h. The solvent was then evaporated, the residue was taken up in $CH_2Cl_2$, and the solution was washed with saturated $NaHCO_3$ solution, dried and again evaporated. The syrup was taken up in warm methanol and the solution was allowed to crystallize. Yield 22.5 g (75% of theory).

The crystals of the triacetyl derivative were suspended in 200 ml of a mixture of methanol, triethylamine and water in the ratio 50:5:5. Solubilization was achieved after stirring for about 40 min. After 1–2 h, the deacetylated glucoside precipitated the preparation, was allowed to stand at 0° C. overnight, and then the precipitate was filtered off and washed with methanol. Additional substance was obtained from the supernatant by repeated precipitation.

Total yield 11 g (65% of theory); melting point: 130° C. Elemental analysis (molecular formula: $C_{16}H_{17}O_{10}N$; molecular weight: 383.315): calculated: C 50.1, H 4.5, N 3.7, O 41.7, found: 49.9, 4.5, 3.7, 41.7.

EXAMPLE 2

3-O-($\alpha$-D-Glucopyranosyl)-2-nitropyridine (compound S2)

Compound S2 was prepared in analogy to compound S1, with the exception that 2H-7-hydroxy-4-methyl-8-nitrobenzopyran-2-one was replaced by 10 g of 3-hydroxy-2-nitropyridine.

Melting point: 178° C. Elemental analysis: calculated: C 43.7, H 4.7, N 9.4, O 42.2, found: 43.7, 4.8, 9.1, 42.5.

EXAMPLE 3

3-O-($\alpha$-D-Galactopyranosyl)-2-nitropyridine (compound S3)

An intimate by blended mixture of 41 g (0.1 mol) of acetobromogalactose and 28 g (0.2 mol) of 3-hydroxy-2-nitropyridine was fused by heating to 70° C., stirring efficiently and with exclusion of moisture. After addition of a mixture of 13 g of $Hg(CN)_2$ and 1 g of $HgBr_2$, the temperature was brought to 100° with stirring (1 h) (HCN evolution). After cooling, 50 ml of ethyl acetate and then 200 ml of $CCl_4$ were added, the solution was treated with 1 g of active charcoal and then filtered through 10 g of silica gel. The filtrate was extracted by shaking with saturated bicarbonate and then with 1N KBr solution, dried and evaporated to dryness. The syrupy residue was dissolved in warm methanol and allowed to crystallize at 0° C.

The crystals of the tetraacetyl compound were suspended in 200 ml of a methanol/triethylamine/water mixture, in the ratio 50/5/5, and dissolution occurred after about 40 minutes stirring. After 1–2 hours, the deacetylated $\alpha$-galactoside separated out. It was allowed to stand at 0° C. overnight, then filtered off and washed with methanol.

Melting point: 220° C.

Elemental analysis (molecular formula): $C_{11}H_{14}O_8N_2$; molecular weight: 302.243: calculated: C 43.7, H 4.7, N 9.2, O 42.3, found: 43.8, 4.8, 9.2, 42.8.

EXAMPLE 4

2H-7-O-($\beta$-D-Glucopyranosyl)-4-methyl-8-nitrobenzopyran-2-one (compound S4)

18 g of 2H-7-hydroxy-4-methyl-8-nitrobenzopyran-2-one + 16 g of acetobromoglucose + 50 g of anhydrous $Na_2CO_3$ were boiled under reflux in 200 ml of acetone for 20 h, then the mixture was filtered, the filtrate was evaporated, the residue was taken up in chloroform, and the solution was washed with 0.1 normal NaOH, dried, evaporated again and the residue was then taken up in methanol, whereupon the tetraacetyl derivative crystallized out. For the deacetylation, the tetraacetyl derivative was stirred with catalytic amounts of sodium methylate in methanol for about 8 h.

Melting point: 210° C.

Elemental analysis: calculated: C 50.1, H 4.5, N 3.7, O 41.7, found: 50.4, 4.6, 3.7, 41.2.

EXAMPLE 5

3-O-($\beta$-D-Glucopyranosyl)-2-nitropyridine (compound S5)

Compound S5 was prepared in analogy to compound S4, the 2H-7-hydroxy-4-methyl-8-nitrobenzopyran-2-one being replaced by 16 g of the silver salt of 3-hydroxy-2-nitropyridine.

Melting point: 206° C.

| Elemental analysis: | | | | |
|---|---|---|---|---|
| | C | H | N | O |
| calculated | 43.7 | 4.6 | 9.2 | 42.3 |
| found | 43.5 | 4.5 | 9.1 | 42.3 |

EXAMPLE 6

Resorufin-8-β-D-galactopyranoside (compound S6)

5 g of resazurin Na were stirred with 8.2 g of acetobromogalactose in acetonitrile for 5 days. After filtration, the solvent was removed and the residue was taken up in ethyl acetate which was extracted by shaking with saturated $NaHCO_3$ solution. After drying, the ethyl acetate was also removed in vacuo, and the residue, composed of resazurin-β-galactoside tetraacetate, was crystallized from methanol. Resorufin-β-D-galactopyranoside was prepared from resazurin-β-D-galactopyranoside tetraacetate by hydrogenation in methanol using palladium/active charcoal as the catalyst.

When the solution was completely colorless, 1 ml of 0.1N sodium methylate in methanol was added to each 100 ml of the solution, and the mixture was stirred for 3 h and filtered through 10 g of silica gel. During evaporation by blowing air through the resorufin-galactoside crystallized. The orange-colored crystals were filtered off after 24 h at 0° C.

Melting point: 222° C.

Elemental analysis: calculated: C 57.6, H 4.6, N 3.7, O 34.1, found: 57.8, 4.9, 3.4, 34.2.

EXAMPLE 7

3-O-(β-D-Galactopyranosyl)-2-nitropyridine (compound S7)

Compound S7 was prepared in analogy to compound S4, the 2H-7-hydroxy-4-methyl-8-nitrobenzopyran-2-one being replaced by 16 g of the silver salt of 3-hydroxy-2-nitropyridine and the acetobromoglucose being replaced by acetobromogalactose.

Melting point: 245° C.

| Elemental analysis: | | | | |
|---|---|---|---|---|
| | C | H | N | O |
| calculated | 43.7 | 4.7 | 9.4 | 42.2 |
| found | 43.7 | 4.6 | 9.3 | 42.1 |

EXAMPLE 8

2H-7-O-(2-Acetamido-3-deoxy-β-D-glucopyranosyl)-4-methyl-8-nitrobenzopyran-2-one (compound S8)

15 g of β-chloro N-acetylaminoglucoside were dissolved together with 6.63 g of 2H-7-hydroxy-4-methyl-8-nitrobenzopyran-2-one in 200 ml of acetone and, after addition of a solution of 2 g of NaOH in a few ml of water, the mixture was stirred at room temperature for 1 day and maintained at 0°–5° C. for a further 5 days. The acetone was removed under reduced pressure, the residue was taken up in $CHCl_3$, and the solution was extracted by shaking with saturated $NaHCO_3$ solution, dried, and the $CHCl_3$ was removed. The residue immediately crystallized on treatment with warm methanol. For the deacetylation, 1 ml of 0.1N Na methylate solution in methanol was used for each 100 ml of solution.

Melting point: 216°–218° C.

Elemental analysis: calculated: C 50.9, H 4.8, N, 6.6, O 37.7, found: 50.1, 4.9, 6.5, 38.1.

EXAMPLE 9

2H-7-O-(1-β-D-Glucuronopyranosyl)-4-methyl-8-nitrobenzopyran-2-one (compound S9)

15 g of compound S4 were oxidized in 300 ml of phosphate buffer, pH 6.8, in a 1.5 l flask equipped with a high performance stirrer, by bubbling through oxygen at room temperature in the presence of 2 g of platinium black for 72 h. After this, the mixture was heated, the catalyst was filtered off with suction, and the filtrate was acidifed and then evaporated to dryness and the residue was extracted with hot ethyl acetate. The desired β-glucuronide crystallized on standing in an ice bath.

Elemental analysis: calculated: C 46.2, H 4.1, N 3.4, O 46.2, found: 45.1, 3.9, 3.2, 44.6.

EXAMPLE 10

2H-7-O-(α-D-Maltotriosyl)-4-methyl-8-nitrobenzopyran-2-one (compound S10)

After incubation of 1 g of compound S1 and 5 g of α-cyclodextrin with cyclodextrin glucosyltransferase in morpholine/ethanesulfonic acid buffer at pH 6.5 for 2–3 days, the products of the transferase reaction were chromatographed on a 150×5 cm column of Bio-Rad P 2 (400 mesh) at 3–5 bar, 30° C. and a flow rate between 120 and 250 ml/h. The eluting agent was degassed water.

The various fractions were collected and freeze-dried.

Elemental analysis: calculated: C 45.5, H 5.5, N 1.8, O 47.3, found: 45.3, 5.3, 1.9, 44.5.

EXAMPLE 11

2H-7-O-(α-D-Maltotetraosyl)-4-methyl-8-nitrobenzopyran-2-one (compound S11)

Compound S11 was prepared in analogy to compound S10, the fractions eluted from the chromatography column after compound S10 being collected and freeze-dried.

HPLC analysis: Elution from a phenyl column supplied by Waters (Bondapak phenyl 10 μm, 3.9×300 mm) was carried out with a mixture of water and methanol in the ratio 70/30 and a flow rate of 1.12 ml/min. Under these conditions, compound S11 was eluted after an elution period of about 7.3 min.

EXAMPLE 12

3-O-(α-D-Maltotriosyl)-2-nitropyridine (compound S12)

Compound S12 was prepared in analogy to compound S10, 1 g of compound S2 being used in place of compound S1.

Elemental analysis: calculated: C 41.6, H 5.7, O 48.3, N 4.2, found: 41.4, 5.6, 46.8, 3.1.

EXAMPLE 13

2H-7-O-(Phosphoryl)-4-methyl-8-nitrobenzopyran-2-one (compound S13)

All reagents must be carefully dried. 12.5 g of 2H-7-hydroxy-4-methyl-8-nitrobenzopyran-2-one were dissolved in 200 ml of pyridine. The solution was added dropwise, with stirring, to a solution of 8.5 g of $POCl_3$ in 20 ml of pyridine. Care was taken during this that the temperature did not exceed 5° C. After 30 minutes, the reaction product was decomposed by addition of ice-water (100 ml). The solution was then adjusted to pH 7.5 by dropwise addition of 10N NaOH, while stirring. Pyridine and water were evaporated under reduced pressure at the lowest possible temperature (50° C. maximum) 30 ml of acetone were added to the residue, which was triturated, and the mixture was extracted with 125 ml of warm 80% by volume aqueous methanol. 300 ml of acetone were added to the methanol solution. The compound S13 was obtained as the disodium salt. Recrystallization from 70% by volume aqueous ethyl alcohol.

EXAMPLE 14

Resorufin phosphate (compound S14)

A solution of 4.5 g of bis-2,2,2-trichloroethylphosphoryl chloride in 50 ml of acetonitrile was added dropwise to 2.5 g (0.01 mol) of sodium resazurin in 50 ml of dry acetonitrile. 5 ml of pyridine were admixed towards the end of the addition of the above solution. The mixture was stirred for 3 h while cooling in an ice bath and for a further 15 minutes at room temperature. The mixture was evaporated under reduced pressure, the residue was taken up in chloroform, the solution was washed with $NaHCO_3$, dried and evaporated, and the residue was crystallized from ethanol. Resorufin phosphate was obtained by reduction of the crystallized product using zinc powder suspended in pyridine, during which the protective groups were also removed.

EXAMPLE 15

3H-7-Hydroxy-9-cyanoxanthen-3-one (cyanorufin; compound C1)

5.5 ml of trifluoroacetic anhydride were added dropwise, at a rate such that the temperature remained below 5° C., to an ice-cooled, stirred solution of 9 g of 3H-7-hydroxy-9-hydroxyiminomethylxanthen-3-one and 11.5 ml of anhydrous pyridine in anhydrous dioxane. After the addition, the mixture was brought to room temperature and stirred for a further 6 h, poured onto 200 ml of ice-cooled 2N HCl, and the precipitate which separated out was filtered off with suction, washed with water and dried. Recrystallization from ethanol. Yield 7.7 g (89.5% of theory).

The melting point of cyanorufin is above 300° C. Cyanorufin has a $pK_a$ of 5.55, the absorption maximum is at 578 nm, and the molar extinction coefficient at 578 nm and pH 7.1 is 64,420 $l.mol^{-1}.cm^{-1}$.

Elemental analysis (molecular formula $C_{14}H_7O_3N$, molecular weight: 237.217): calculated: C 70.9, H 3.0, O 20.7, N 5.9, found: 69.6, 3.6, 20.7, 5.3.

The advantages of this new chromogen are its low $pK_a$, its very high extinction coefficient and its absorption in the long-wavelength region.

EXAMPLE 16

Preparation of N-toluenesulfonyl-L-alanine (tosylalanine)

0.01 mol of L-alanine were dissolved in 20 ml of 1-molar sodium hydroxide solution, a solution of 0.01 mol of p-toluenesulfonyl chloride in 10 ml of diethyl ether was added, and the mixture was vigorously stirred for 4 h. The ether phase was separated off, and the aqueous phase was acidified to pH 3 with concentrated hydrochloric acid. The crude n-toluenesulfonyl-1-alanine started to crystallize (cooling to 4° C. where necessary) and was filtered off and recrystallized from 60% by volume aqueous alcohol. Melting point 130°–131° C.

EXAMPLE 17

Preparation of tosylalanylresorufin 220 mg (1.1 mmol) of dicyclohexylcarbodiimide, 165 mg (1.1 mmol) of 1-hydroxybenzotriazole and 1 mmol of tosylalanine were dissolved in 5 ml of dimethylformamide (DMF) at room temperature, with stirring. Then 210 mg (1 mmol) of resorufin (supplied by Aldrich, USA) were added, and the mixture was stirred for a further 2 h. The mixture was subsequently added to 100 ml of ice-water and extracted by shaking with 250 ml of ethyl acetate. After separation, the ethyl acetate phase was dried with sodium sulfate and the ethyl acetate was removed under reduced pressure.

The product purified by column chromatography (column: silica gel; mobile phase: $CHCl_3 + CH_3OH$ 9:1) had a melting point of 165° C. and was pure by thin layer chromatography.

EXAMPLE 18

Preparation of Tos-Gly-Pro-Arg-resazurin 1 mmol of Tos-Gly-Pro-Arg-OH was suspended in 30 ml of tetrahydrofuran (dry). 4 mmol of ethyl chloroformate were added at room temperature, and the mixture was stirred for about 15 minutes and cooled to −10° C. 3 mmol of N-methylmorpholine were added and the mixture was stirred at room temperature for 60 minutes. 3 mmol of resazurin in 60 ml of desiccated tetrahydrofuran were then admixed dropwise. The reaction was complete after 4 h and the mixture was filtered and the filtrate was evaporated.

The crude product was purified on a chromatography column (stationary phase: silica gel; mobile phase: $CHCl_3 +$ glacial acetic acid 19:1). A test paper which has been impregnated with a ethanol solution cintaining 0.01% of this substrate and dried thereafter produces immediate blue-violet coloration on moistening with a blood plasma solution.

EXAMPLE 19

Determination of the alpha-amylase activity using compound S10

585 mg of NaCl and 200 mg of compound S10 were dissolved in 100 ml of M/15 phosphate buffer, pH 6.0. 20 μl of urine were pipetted into 1 ml of this solution which was thoroughly mixed. The change in absorbance at 365 nm was continuously recorded in a photometer with a pen recorder attached. The change in absorbance per miute (delta A/min) was calculated from the recording on the pen recorder, and the enzyme activity (U/L) was calculated using the following formula:

$$U/L = \frac{\text{delta } A/\text{min} \times 1.02 \times 1000}{0.02 \times 16.1}$$

$$= \text{delta } A/\text{min} \times 3168$$

1.02 = assay volume including the sample, in ml
0.02 = sample volume in ml
1000 = conversion factor from ml to l
16.1 = extinction coefficient of 2H-7-hydroxy-4-methyl-8-nitrobenzopyran-2-one at pH 6.0 and 365 nm, in $cm^2/\mu mol$.

Other hydrolases can be determined analogously using one of the substrates according to the invention which is specific for the enzyme with appropriate reaction conditions.

EXAMPLE 20

Determination of leukocyte esterase using tosylalanylresorufin

Indicator paper No. 218 supplied by Macherey-Nage, Dueren, Federal Republic of Germany, was impregnated successively with the following solutions and was dried:

(a) aqueous boric acid buffer 0.25 mol/l, pH 8
(b) tosylalanylresorufin 0.25 g dissolved in 1 l of ethyl acetate.

The drying temperature selected for solution (a) was about 80° C. and that for (b) was about 120° C. The samples used were suspensions containing various concentrations of leukocytes, into which the test strips were briefly immersed. After about 1 minute a red-violet color developed, the intensity of which depended on the concentration of leukocytes. The detection sensitivity of this test system is about 1000 leukocytes per microliter.

When n-tosylaminobutyryl or Boc-Leu-resorufin was used in impregnating solution (b), the test papers obtained had detection sensitivities of 1000 and 2000 leukocytes per microliter respectively.

EXAMPLE 21

Preparation of 2H-7-O-(β-Galactopyranosyl)-4-methyl-8-nitrobenzo-pyran-2-one, compound S15

Compound S15 was prepared in analogy to compound S4, but 16 g of acetobromogalactose were used in place of the acetobromoglucose.

Melting point: 188°–192° C.

| | Elemental analysis: | | | |
|---|---|---|---|---|
| | C | H | N | O |
| calculated | 50.1 | 4.5 | 3.7 | 41.7 |
| found | 50.2 | 4.6 | 3.7 | 41.3 |

We claim:

1. A compound of the formula A—O—B, in which A represents the radical in the ion A—O⁻ of a heterocyclic compound A—OH with an acid p$K_a$, whose absorbance is measured photometrically after hydrolysis of A—O—B, while B is the radical in a compound B—OH which makes the compound specific for the reaction with a given enzyme, and where A—OH is selected from the group consisting of:

a. a compound of the formula I

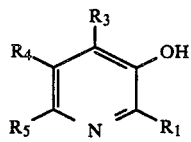

in which $R_1$ can be OH, $NO_2$ or halogen, and $R_3$, $R_4$ and $R_5$ can be H or $NO_2$, at the most two $NO_2$ being present, b. a compound of the formula II

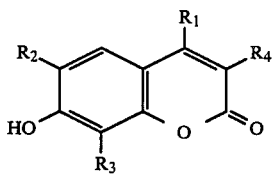

in which $R_1$ can be H or alkyl with 1–12 carbon atoms, and $R_2$, $R_3$ or $R_4$ can be H or $NO_2$, one or two $NO_2$ being present, c. a compound of the formula III

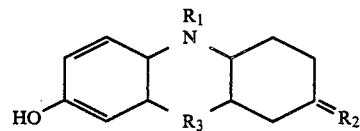

in which $R_1$ can be 0 or an electron pair, $R_2$ can be O, S or N(CH$_3$)$_2$, and $R_3$ can be O or S and d. a compound of the formula IV

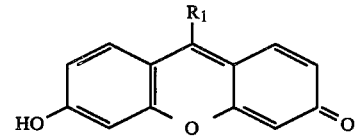

in which $R_1$ can be aryl, and B—OH is a sugar or sugar derivative.

2. A compound of the formula II according to claim 1, identified by the name 2H-7-O-(β-D-Maltotriosyl)-4-methyl-8-nitrobenzopyran-2-one.

3. A compound of the formula A—O—B, in which A represents the radical in the ion A—O⁻ of a heterocylic compound A—OH with an acid p$K_a$, whose absorbance is measured photometrically after hydrolysis of A—O—B, while B is the radical in a compound B—OH which makes the compound specific for the reaction with a given enzyme, and where A—OH is a compound of the formula II

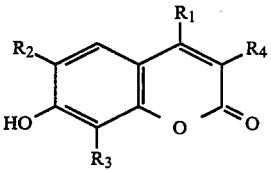

in which $R_1$ can be H or alkyl with 1–12 carbon atoms, and $R_2$, $R_3$, or $R_4$ can be H or $NO_2$, one or two $NO_2$ being present, and B—OH is a sugar or sugar derivative.

4. A compound according to claim 3, wherein $R_1$ is H or alkyl with 1–3 carbon atoms, B—OH is glucose, a multidextrin, galactose, glucuronic acid, N-acetyl-glucosamine or fucose.

5. A compound of the formula II according to claim 1, identified by the name 2H-7-O-(alpha-D-Glucopyranosyl)-4-methyl-8-nitrobenzo-pyran-2-one.

6. A compound of the formula II according to claim 1, identified by the name 2H-7-O-(beta-D-Glucopyranosyl)-4-methyl-8-nitrobenzo-pyran-2-one.

7. A compound of the formula II according to claim 1, identified by the name 2H-7-O-(2-Acetamido-3- deoxy-beta-D-glucopyranosyl)-4-methyl-8-nitrobenzopyran-2-one.

8. A compound of the formula II according to claim 1, identified by the name 2H-7-O-(1-beta-D-Glucuronopyranosyl)-4-methyl-8-nitrobenzopyran-2-one.

9. A compound of the formula II according to claim 1, identified by the name 2H-7-O-(alpha-D-Maltotriosyl)-4-methyl-8-nitrobenzo-pyran-2-one.

10. A compound of the formula II according to claim 1, identified by the name 2H-7-O-(beta-D-Maltotetraosyl)-4-methyl-8-nitro-benzo-pyran-2-one.

11. A compound of the formula II according to claim 1, identified by the name 2H-7-O-(beta-Galactopyranosyl)-4-methyl-8-nitrobenzopyran-2-one.

12. A compound according to claim 1, wherein in formula II $R_1$ is H or alkyl with 1-3 carbon atoms, in formula IV aryl is phenyl, CN or alkyl with 1-12 or 13 carbon atoms, and B—OH is glucose, a maltodextrin, galactose, glucuronic acid, N-acetylglucosamine or fucose, the protective group is toluenesulfonyl or a compound selected from the carbobenzyloxy (CBZ) group such as N-tosylalanine or CBZ-glycine.

* * * * *